United States Patent [19]

Shaw et al.

[11] 4,394,045
[45] Jul. 19, 1983

[54] SPORTSMAN SLING SEAT AND GAME HAUL

[76] Inventors: Jack B. Shaw, 2710 Bedford St.; Donald E. Shaw, 101 Merchant St., both of Johnstown, Pa. 15904

[21] Appl. No.: 214,992

[22] Filed: Dec. 10, 1980

[51] Int. Cl.³ .............................................. A47C 13/00
[52] U.S. Cl. ..................................... 297/118; 297/217
[58] Field of Search ............... 297/118, 217, 452, 457; 182/187

[56] References Cited

U.S. PATENT DOCUMENTS

| | | | |
|---|---|---|---|
| 2,549,679 | 4/1951 | Foote | 248/218.4 X |
| 2,722,968 | 11/1955 | Smith | 297/457 |
| 2,821,335 | 1/1958 | White | 297/217 X |
| 2,847,059 | 8/1958 | Klins | 182/187 X |
| 2,851,085 | 9/1958 | Woodward | 182/187 X |
| 3,992,055 | 11/1976 | Shaw et al. | 297/217 |
| 4,315,655 | 2/1982 | Machnik | 297/118 |

*Primary Examiner*—Francis K. Zugel
*Attorney, Agent, or Firm*—Fidelman, Wolffe & Waldron

[57] ABSTRACT

A collapsible seat for attachment to a vertical support and adapted for use without modification as a game pull or arm sling. The seat includes a strap for encompassing a vertical support and a seat member of trapezoidal shape of a flexible material such as canvas. Webbing straps extend along the parallel bases of the trapezoidal seat and are joined at a distance from the seat sides to form a loop through which the strap passes for attachment to a vertical support.

3 Claims, 4 Drawing Figures

SPORTSMAN SLING SEAT AND GAME HAUL

BACKGROUND OF THE INVENTION

This invention relates generally to multi-purpose collapsible seats.

More specifically this invention relates to a collapsible, easily portable sportsman's seat adaptable for use without modification as a game pull or arm sling.

A number of portable and collapsible seats have been developed for use by sportsmen, particularly hunters. Such seats are typically designed for attachment to objects such as trees to provide a safe and comfortable place to sit particularly in inclement weather. U.S. Pat. Nos. 2,549,679; 2,722,968; 2,847,968 and 3,992,055 are considered to be representative of approaches taken in the prior art in the construction of such seats. Many of the collapsible seats of the prior art have included rigid parts which increase the bulk of the seat and make it difficult to assemble and transport. Others, illustrated particularly by U.S. Pat. No. 3,992,055, have provided seat designs which eliminate all rigid parts but are useful only for seating purposes.

A multi-purpose seat design, illustrated in U.S. Pat. No. 2,821,335, has been proposed. The device illustrated in that patent includes a convertible member which may be utilized in forming a seat, as a game receptacle or as a support member for a game tow line. When used in the latter mode, the seat member is disposed across the chest of a hunter with a strap arranged around the hunter's neck to hold the device in place. This arrangement does not provide for optimum coupling between the hunter and the load being pulled as the rigid reinforcing members disposed at the ends of the seat member require that the seat member be positioned too low across the chest for efficient hauling.

SUMMARY OF THE INVENTION

This invention provides a simple, easily fabricated multi-use device which without modification may function as a collapsible chair, a game pull or an arm sling. A trapezoidal piece of flexible material, suitably a heavy fabric, is provided with webbing straps extending along and beyond the parallel bases of the trapezoidal piece. The straps are joined at a distance from the sides of the trapezoidal piece to form loops through which a strap may be passed. The strap may be fixed around a vertical support, such as a tree, to form a chair. The device is used as a game pull by placing the trapezoidal piece across the chest with the short base of the trapezoid upward, passing one pair of straps over the shoulders and the other pair beneath the arms. For use as a sling, the trapezoidal piece is folded with the webbing strap loops together. The user's head is then slipped between the webbing straps with the loops arranged generally at the back of the neck. Position of the sling may be adjusted by use of a single knot tying the webbing pairs together.

Hence, it is an object of this invention to provide a multi-use device which may function as a collapsible chair, a game pull, or an arm sling.

It is another object of this invention to provide a collapsible sportsman's implement of simple construction fabricated without use of rigid elements.

Other objects, advantages, and novel features of this invention will be apparent from the following detailed description when considered in conjunction with the accompanying drawing.

DESCRIPTION OF THE PREFERRED EMBODIMENTS

Figure 1:
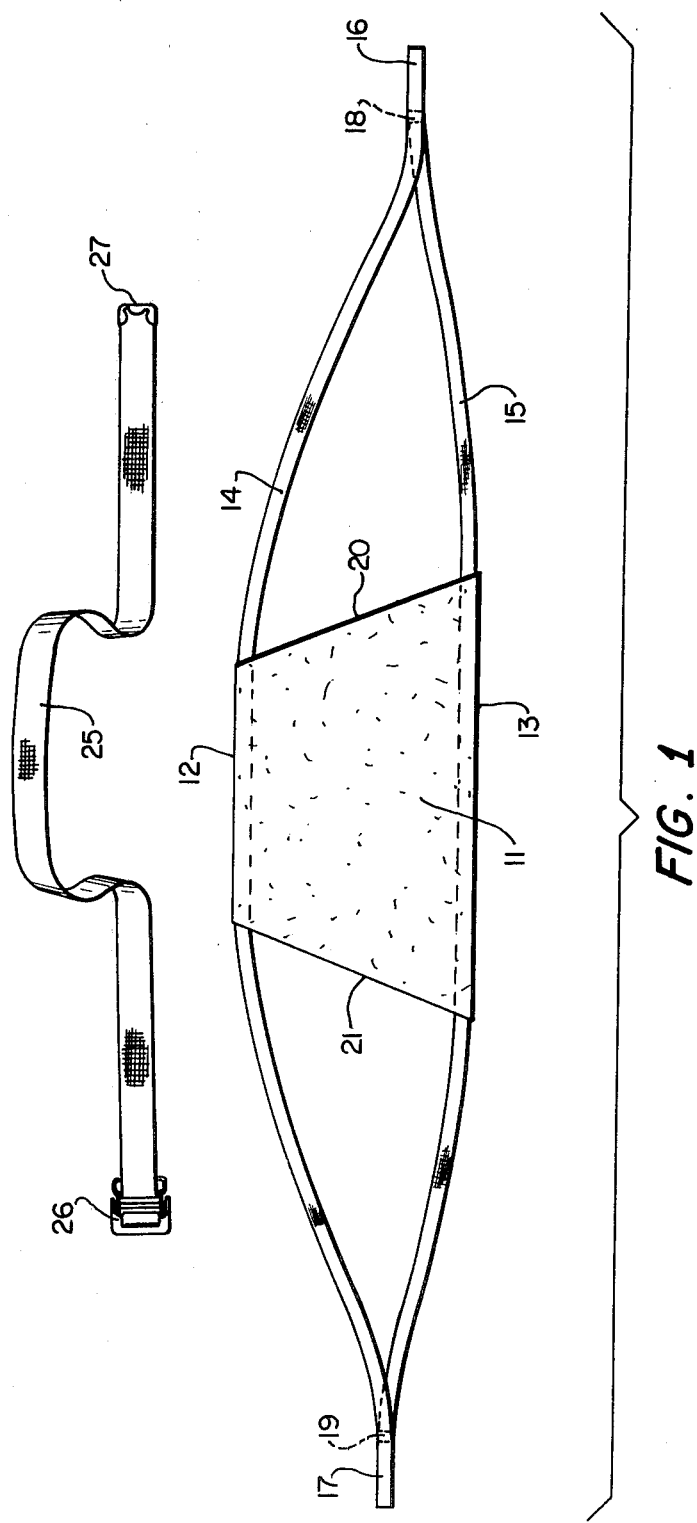
FIG. 1 is a plan view of the multi-use implement of this invention.

Referring first to FIG. 1, there is shown the components of the multi-use chair, game pull and arm sling. Trapezoidal member 11, which functions in the different modes of use as a chair seat, chest harness and arm sling, is made of a single piece of flexible material, preferably of woven fabric such as canvas, nylon or the like. Member 11 is of regular trapezoidal shape having an upper base 12 and a lower parallel base 13. The dimensions of member 11 are critical to proper functioning of the device in its various modes. The ratio of the length of upper base 12 to the length of lower base 13 may vary from about 0.45 to 0.70 while the distance between upper base 12 and lower base 13, measured perpendicularly, may vary from about 0.7 to about 1.2 the length of base 12.

In actual dimension, upper base 12 must be relatively close to the chest width of the user or generally within the range of about 12 to about 16 inches. Lower base 13 must be proportioned to the upper base within the aforesaid ratios to make member 11 useable as a seat and to provide comfort to the user in the game pull mode. Length of the lower base 13 may range generally from about 22 to about 26 inches while the distance between the upper and lower bases may range from about 11 to 15 inches.

Webbing strap 14 extends along the length of upper base 12 and continues outwardly for a distance beyond both ends of base 13. Likewise, webbing strap 15 extends along the length of lower base 13 and continues outwardly for a distance beyond both ends of the base where it is joined to strap 14 to form loops 16 and 17. Webbing straps 14 and 15 are preferably attached to member 11 by stitching. Stitching may also be used in a patch pattern 18 and 19 to join the webbing straps to form the loops. Sides 20 and 21 of member 11 may be hemmed by stitching to prevent the fabric from raveling.

Figure 2:
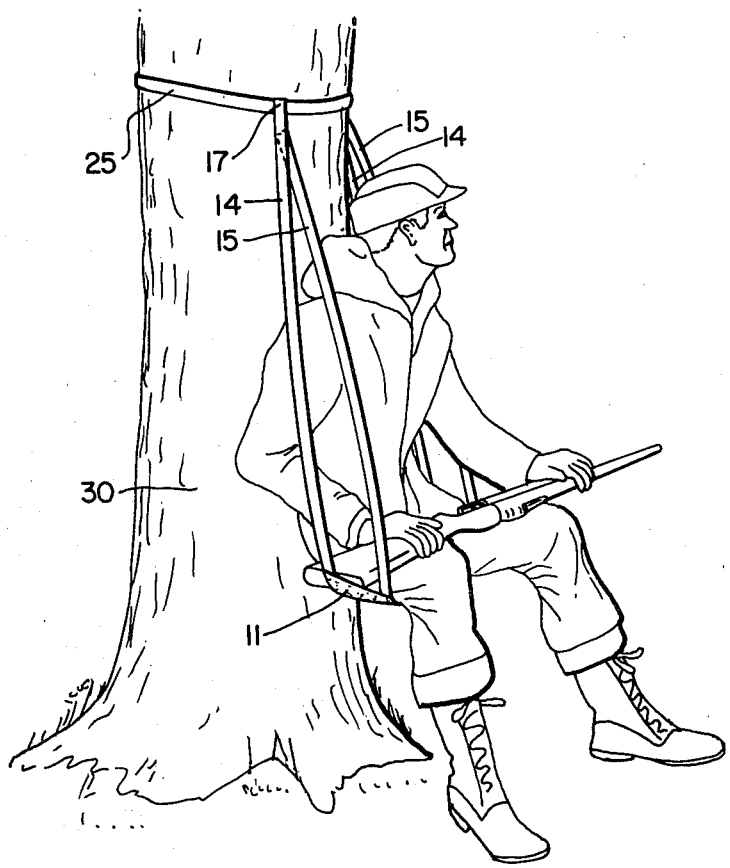
FIG. 2 depicts the implement functioning as a collapsible chair.

Belt member 25, preferably constructed of standard webbing stock, is equipped with buckle 26 and end member 27. Loops 16 and 17 are dimensioned so as to allow free passage of belt 25 through them for use in forming a chair, shown in FIG. 2, or to provide a tow line in the game pull mode shown in FIG. 3. As is illustrated in FIG. 2, belt 25 is passed through loops 16 and 17 and encircles a vertical support such as tree 30. The upper base 12 is disposed inwardly adjacent the vertical support, thus providing an outwardly flaring seat portion formed by member 11.

Figure 3:
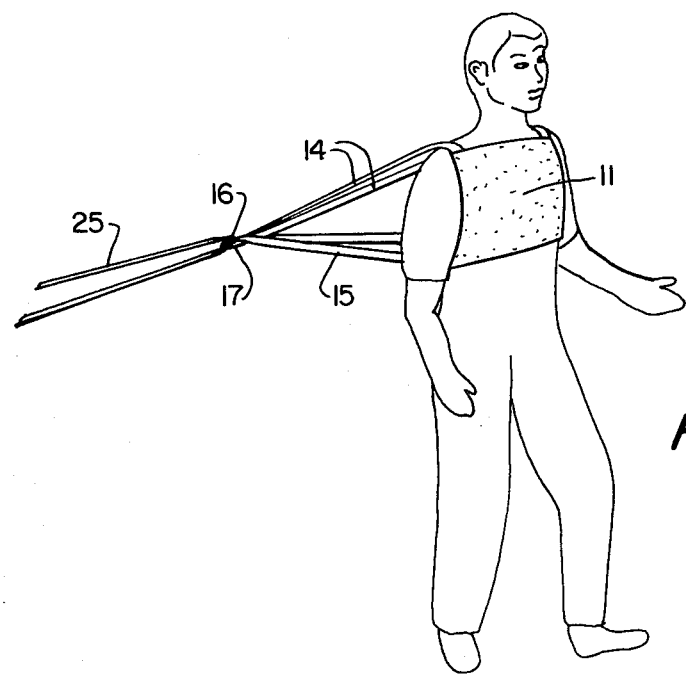
FIG. 3 illustrates use of the implement as a game pull or similar use.

FIG. 3 illustrates the implement used as a game tow. The user's arms are slipped between webbing straps 14 and 15 as shown with the upper base 12 of member 11 adjusted to fit along a line approximating the top of the shoulders. Webbing straps 14 pass backwardly over the top of the user's shoulders while webbing straps 15 pass backwardly from the user's lower chest and the two loops 16 and 17 are brought together for attachment to belt 25 which in turn is attached to the object under tow.

The criticality of the dimensions of trapezoidal member 11 may be fully appreciated when contemplating the use of the implement in this mode. The upper base 12 must be dimensioned so as to approximate the chest width of the user so that webbing straps 14 pass backwardly over the shoulders. Lower base 13 must be longer than is the upper base so as to distribute the pull exerted over the full chest area. The distance between upper base 12 and lower base 13 must not be so great that webbing 15 drops below the rib cage of the user.

Figure 4:
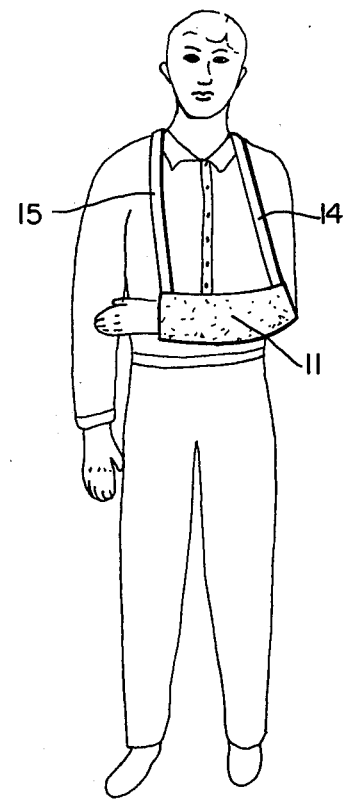
FIG. 4 illustrates use of the implement as an arm sling.

FIG. 4 illustrates use of the device as an arm sling to provide support for an injured or broken arm. In this use mode, member 11 forms a cradle for the forearm while webbing straps 14 and 15 are passed upwardly over the user's shoulders to form a loop behind his head. Vertical adjustment of the sling position can be made by knotting the webbing straps at an appropriate position.

The trapezoidal member 11 with its attached webbing straps 14 and 15 may be rolled up into a compact form for carrying. Belt 25 may be wrapped around that rolled form and secured. As may be seen, the multi-use device of this invention is highly portable, light in weight and easily carried in a pocket or worn around the waist of a sportsman.

From the preceding description of the preferred embodiments, it is evident that the objects of this invention are attained. Although the invention has been described and illustrated in detail, it is to be clearly understood that the same is by way of illustration and is not to be taken as limitation.

I claim:

1. A multi-use sportman's implement comprising:
   seat means for providing a seat for a user when suspended from a support;
   sling means for supporting a user's arm when suspended from the neck of said user;
   chest means for distributing towing forces across the chest of said user when used for towing game;
   said seat, sling, and chest means comprising a trapezoidal-shaped member, fabricated of flexible material, having an upper base and a lower base, said upper base having a length approximating the width of a man's chest and said lower base having a length greater than said upper base length;
   first and second strap means respectively disposed and stitched along said upper and lower bases and extending outwardly from a first side and a second side of said trapezoidal-shaped member, said strap means extending from said first side being continuous from said upper base to said lower base and stitched together distal from said first side to provide large and small loops, and said strap means extending from said second side being continuous from said upper base to said lower base and stitched together distal from said second side to provide large and small loops;
   a flat belt slidably receivable through said small loops, said belt adjustably attachable to said support when using said implement as a seat, and to said game when using said implement for game towing such that said user's arms are respectively inserted through said large loops of said first and second sides with said chest means against said user's chest and each of said first strap means across a shoulder of said user to suspend said chest means; and
   said large loops passable over said user's head to suspend said sling means from said neck when said implement is used as an arm sling.

2. The implement of claim 1 wherein the ratio of the length of said upper base to the length of said lower base ranges from about 0.45 to about 0.70.

3. The implement of claim 1 wherein the distance between said upper base and said lower base, measured perpendicularly, ranges from about 0.7 to about 1.2 times the length of the upper base.

* * * * *